United States Patent [19]

Bertelli et al.

[11] Patent Number: 4,798,857

[45] Date of Patent: Jan. 17, 1989

[54] COMPLEXES OF BISMUTH OR ANTIMONY HALIDES WITH AMINES, SUITABLE AS FLAME RETARDANTS FOR POLYMERS, AND POLYMER COMPOSITIONS CONTAINING SAME

[75] Inventors: Guido Bertelli, Ferrara; Patrizia Busi, Portomaggiore; Renato Locatelli, Ferrara, all of Italy

[73] Assignee: HIMONT Incorporated, Wilmington, Del.

[21] Appl. No.: 139,420

[22] Filed: Dec. 30, 1987

[30] Foreign Application Priority Data

Dec. 30, 1986 [IT] Italy ............................ 22887 A/86
Dec. 30, 1986 [IT] Italy ............................ 22888 A/86

[51] Int. Cl.$^4$ .......................... C08K 5/34; C08K 5/31; C07F 9/90; C07F 9/94
[52] U.S. Cl. ................................ 524/93; 252/609; 524/100; 524/177; 524/204; 524/410; 544/181; 544/225; 548/107; 548/108; 548/404; 556/35; 556/36
[58] Field of Search .............. 524/93, 100, 177, 204, 524/410; 556/35, 36; 544/225, 181; 548/404, 107, 108; 252/609

[56] References Cited

U.S. PATENT DOCUMENTS 3,280,030 10/1966 Kay et al. ..................... 252/49.6
3,705,128 12/1972 Knowles ........................ 524/97
3,850,882 11/1974 Underwood et al. ............ 524/430
4,028,333 6/1977 Lindvay ........................ 524/100
4,203,882 5/1980 Bertelli et al. ................. 524/100
4,264,364 4/1981 Lippoldt ....................... 524/204

OTHER PUBLICATIONS

CA 68: 110113a (1968).
CA 75: 122896r (1971).
D. Bauer and J. P. Beck–Electroanalytical Chemistry and Interfacial Electrochemistry–32 (1971) 21-34.

Primary Examiner—Veronica P. Hoke

[57] ABSTRACT

Disclosed are complexes of bismuth or antimony halides with amines having formula:

R•(MeX$_3$)y,

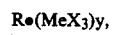

where R is dicyandiamide, guanamine, 2-guanidinobenz-imidazole, isophoronediamine, piperazine, melamine or a compound having from 2 to 9 triazine rings condensed or linked to each other through at least one —NH— group; Me is Bi or Sb; X is chlorine or bromine; and y is a number from 0.3 to 4. Processes for preparing the complexes and flame retardant thermoplastic polymer compositions containing the complexes are also disclosed.

20 Claims, No Drawings

COMPLEXES OF BISMUTH OR ANTIMONY HALIDES WITH AMINES, SUITABLE AS FLAME RETARDANTS FOR POLYMERS, AND POLYMER COMPOSITIONS CONTAINING SAME

The present invention referes to new complexes of Bi and Sb halides suitable as flame retardants of thermoplastic polymers and to the polymer compositions containing said complexes.

Compositions suitable for imparting flame-resistance to polymers are known in the art, which comprise thermally unstable halogenated organic compounds and metal compounds, in particular compounds of antimony and/or bismuth. The extinguishing action in this case is attributed to the metal halide which is formed during the combustion.

In other cases the metal halide is already present in the self-extinguishing composition, for instance in the form of double salts of ammonium and metals.

However, it is known that ammonium salts cannot be employed as additives in polymers, due to their high corrosivity and the excessive sensitivity to water and heat.

In place of the ammonium salts, it is known to use organic compounds containing nitrogen, such as melamine and melamine bromohydrate, which, beside overcoming the above mentioned drawbacks of the double salts, form, during the combustion, carbonaceous residues capable of arresting the flame. A solution of this kind is described in U.S. Pat. No. 4,028,333 in which there are described compositions containing melamine hydrohalides and an antimony and/or bismuth oxide or halide.

This invention provides novel complexes of Bi and Sb halides with amines which give superior flame selfextinguishing properties to thermoplastic polymers when they are added to same in ecceptionally low amounts.

The complexes of the present invention are represented by the formula:

$$R \bullet (MeX_3)_y \qquad (I)$$

where R is an amine selected from the group consisting of dicyandiamide, guanamine, 2-guanidinobenzimidazole, melamine, isophoronediamine, piperazine, all of which may be optionally substituted with an alkyl, aryl or acyl group, and compounds containing from 2 to 9 triazine rings condensed or linked to each other through at least a —NH— group;
Me is bismuth or antimony;
X is chlorine or bromine; and
y is a number comprises from 0.3 to 4.

In the above complexes more than 1 and up to 3 moles of amine can be bound or coordinated to 1 mole of the metal halide. The amine can be the same or different.

Representative examples of amines having triazine rings are the compounds normally obtainable by pyrolysis of melamine, known as "melam", "melem" and "melon" for which the following formulae generally are proposed: (see "Proceedings of the Second European Symposium on Thermal Analysis, University of Aberdeen, U.K., 1–4 Sept. 1981, Editor David Dollimore)

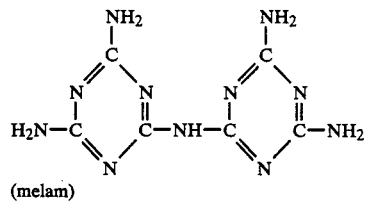
(melam)

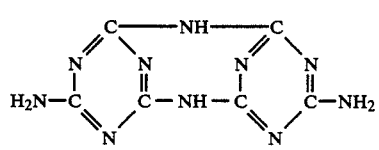

or:

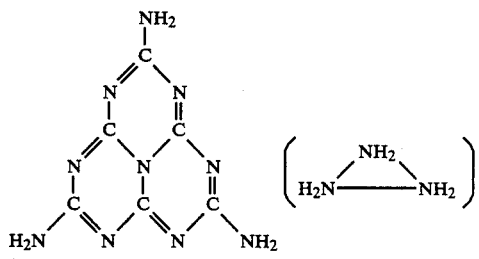
(melem)

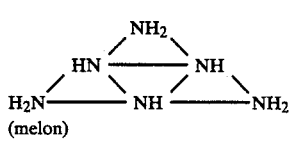
(melon)

The complexes can be prepared by heating at temperatures between 50° and 150° C., a mixture of the amine and the metal halide, using at least 0.3 mole of metal halide per mole of amine or per mole of primary amino groups present in the amino compound.

When dycyandiamide is used, a melting of the mixture of the amine and the metal halide already occurs at about 50° C.

As the temperature is increased up to 130°-150° C., the mixture hardens and the reaction can be considered complete.

According to another method, a solution of the metal halide (for example a solution of the metal halide in an alcohol or a ketone) is gradually added, while stirring, to a solution or suspension of the amine in a chemically inert liquid solvent or suspending agent, for example a hydrocarbon, such as hexane or heptane, at a temperature between 0° C. and 100° C., and then recovering the product, for example by filtration or removal of the solvent. If the amine present in the complex is dicyandiamide or a triazine, the cyclization of dicyandiamide to triazine rings and/or the polycondensation of the triazine up to the desired number of triazine rings can be obtained by heating the complex at a temperature in the range from 100° C. to about 300° C. or more.

It is therefore possible, starting from dicyandiamide or melamine to first prepare the complex with the metal halide and then heat-treating said complex to obtain the cyclization of dicyandiamide to triazine rings and/or the condensation of the triazine rings through —NH— bridging groups or through a direct condensation of the rings.

According to this method complexes with amines of different nature can thereby be obtained in a single preparation.

When the amine contains primary amino groups, from the elemental analysis, the X-ray diffraction spectra and the I.R. analysis, it is possible to show that the metal halide is bound to one or more of said —NH$_2$ groups.

As indicated, the new complexes are suitable as flame retardants for thermoplastic polymers.

Another embodiment of the present invention is therefore represented by the polymer compositions endowed with flame self-exinguishing properties containing said complexes.

The compositions comprise (by weight):
(a) 85–99.7% of a thermoplastic polymer;
(b) 0.3–15% of a complex or a mixture of complexes having the above described formula (I); and
(c) 0–1% of a free radical promoter.

Preferably, the amount of component (b) is comprised between 0.3 and 10% by weight and, more preferably, between 0.3 and 3% with the proviso that, when (c) is not present, component (b) is present in an amount of at least 3% by weight.

Examples of thermoplastic polymers which can be used with the complexes of the present invention are crystalline olefin polymers such as for instance polypropylene, propylene modified with copolymerized ethylene, mixtures of polypropylene with up to 20% by weight of elastomeric ethylene/propylene copolymers containing up to 50% by weight of copolymerized ethylene, elastomeric ethylenepropylene copolymers, polystyrene (crystal grade and high impact), ABS, polyamide and polyester resins.

Preferably a complex (b) is used in which the amine is selected from dicyandiamide, guanamine, melamine and the products of cyclization of dicyandiamide and of condensation of melamine. Satisfactory results, however, have been obtained also with complexes in which the amine is isophoronediamine, 2-guanidinobenzimidazole and piperazine.

Examples of free radical promoters are 2,3-dimethyl-2,3-diphenyl butane and 2.3-dimethyl-2,3-diphenyl hexane.

These non-peroxide free radical promoters, when present, are used in an amount from 0.1% to about 1% by weight with respect to the total composition.

Organic peroxides can also be used as source of free radicals in the present compositions, preferably in amounts ranging between 0.05 and 0.1 parts by weight.

The complex (b), ground to a size of few microns, is also suitable for improving the flame resistance of fibers, raffia and in general of fabrics prepared from polypropylene or other spinnable thermoplastic polymers.

The compositions of the present invention can be prepared according to conventional methods, for instance by mixing the polymer with the additives in a Banbury mixer at a temperature equivalent to or exceeding the polymer softening temperature and then by extruding the mixture in an extruder at the most suitable temperature and then pelletizing. These compositions are suitable for preparing formed articles like films, raffia, chairs, to be used in applications in which flame resistance is required.

Other features, advantages and embodiments of the invention disclosed herein will be readily apparent to those exercising ordinary skill after reading the foregoing disclosures. In this regards, while specific embodiments of the invention have been described in considerable detail, variations and modifications of these embodiments can be effected without departing from the spirit and scope of the invention as described and claimed.

The following examples illustrate the preferred embodiments of this invention.

EXAMPLE 1

This example illustrates a complex of this invention and a method of preparing same.

To a 1-liter glass flask 450 g of bismuth tribromide previously mixed with 90 g of dicyandiamide are introduced.

The flask is hooked to a rotovapor apparatus, heated in an oil bath at 60°–70° C. and made to rotate at this temperature until the mixture is melted.

The temperature is then raised up to 130°–150° C. until completion of the reaction, which is when the contents of the flask are hardened.

When said hardening is obtained, the product is taken out of the flask and milled to fine powder.

Said product, having empirical formula $C_2H_4N_4 \cdot BiBr_3$, is predominantly a complex of 1 mole of dicyandiamide and 1 mole of $BiBr_3$, and has a melting temperature higher than 300° C. In order to provide the complex with stability towards moisture, the complex is then mixed with stearic acid in an amount of 5% by weight in a turbomixer.

In the mixing step stearic acid melts as a result of the friction of the mixing. The product is then cooled and recovered.

EXAMPLE 2

Using the same procedure as in Example 1, 315 g of bismuth trichloride are reacted with 90 g of dicyandiamide.

The resultant product has an empirical formula $C_2H_4N_4 \cdot BiBl_3$ and is predominantly a complex of 1 mole of dicyandiamide with 1 mole of $BiCl_3$.

Its melting point is 280° C.

EXAMPLE 3

Using the same procedure as in example 1, 360 g of antimony tribromide are reacted with 90 g of dicyandiamide.

The resultant product has an empirical formula $C_2H_4N_4 \cdot SbBr_3$ and is predominantly a complex of 1 mole of dicyandiamide and 1 mole of $SbBr_3$.

Its melting point is 220° C.

EXAMPLE 4

Using the same procedure as in of example 1, 450 g of bismuth tribromide are reacted with 130 g of melamine.

The resultant product has an empirical formula $C_3H_6N_6 \cdot BiBr_3$ and is predominantly a complex of 1 mole of melamine and 1 mole of $BiBr_3$.

Its melting point is 290° C.

EXAMPLE 5

This example illustrates another method of preparing the complexes of this invention.

Into a 2 liter, three-necked flask, equipped with mechanical stirrer and reflux condenser, and immersed in an oil bath heated at 110° C. are introduced 90 g of dicyandiamide in dispersion which is maintained in dispersion by strong stirring in 1 liter of xylene. A solution of 450 g of bismuth tribromide in 300 ml of methanol is then added drop wise. After having completed the addition, the condenser is removed and the alcohol is removed by distillation. The product obtained is allowed to cool down, then filtered and dried at 130°–150° C.

The result product has the empirical formula:

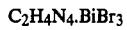

$$C_2H_4N_4 \cdot BiBr_3$$

and is predominantly a complex of 1 mole of dicyandiamide and 1 mole of BiBr$_3$.

In this case, macroscopically the product is a fine powder with small aggregates which are easily broken up.

EXAMPLE 6

Into 2 liter, three-necked flask equipped with mechanicl stirred and reflux condenser and immersed in an oil bath heated at 110° C. are introduced 250 g of melamine in dispersion which is maintained in dispersion by strong stirring in 1 liter of n-heptane. A solution of 450 g of bismuth tribromide in 300 ml of acetone is then added drop wise. After completing the addition, the condenser is removed and the acetone was removed by distillation. The resultant product is allowed to cool, then it is filtered and dried at 120°–130° C. under low pressure and a nitrogen flow.

The resultant product has the empirical formula:

$$2C_3H_6N_6 \cdot BiBr_3$$

and is predominantly a complex of 2 moles of melamine and 1 mole of BiBr$_3$.

Its melting point is 290° C.

In this case, macroscopically the product is a fine powder with small aggregates which are easily broken up.

EXAMPLE 7

The product obtained according to example 6 is subjected to further thermal treatment in a muffle at 300° C. for the time sufficient to result in a 10% decrease in weight of the product.

The resultant product has a melting point at about 380° C. and shows, by the quantitative analysis, a decrease in the content of nitrogen and hydrogen.

From the quantitative analysis, the IR analysis and the X-ray diffraction, the resultant product has a predominantly amorphous structure and has the characteristic absorption bands of "melam", "melem" and "melon".

EXAMPLE 8

Using the same procedure as in example 6, 362 g of antimony tribromide are reacted with 125 g of acetoguanamine.

The product has empirical formula:

$$C_4H_7N_5 \bullet SbBr_3$$

and is predominantly formed of a complex of 1 mole or acetoguanamine with 1 mole of SbBr$_3$.

TABLES 1–4

In tables 1–4 there are reported examples of selfextinguishing polymer compositions of this invention obtained by employing as additives the complexes prepared according to examples 1–8.

Said compositions are prepared as previously described, using a Dolci extruder with a 20 mm diameter screw, length/diameter ratio of the screw =23 and screw operating speed =20 r.p.m., at a temperature of 200°–240° C.

In order to evaluate the self-extinguishing properties of the compositions, 3 mm-thick test pieces are molded from the granular product by means of a Carver molding machine, operating at a temperature at least corresponding to the polymer softening temperature, at 40 Kg/cm$^2$ pressure for 7 minutes.

The degree of flame resistance is determined on said test pieces by means of the "Oxygen Index" measure (according to ASTM-D2863 test specification), which gives the minimum percentage of oxygen in mixture with nitrogen necessary for the sample to burn continuously, as well as by complying with UL-94 specifications (published by Underwriters Laboratories - USA) which provide an evaluation of the degree of extinguishment of plastic materials. In applying such specifications, the "Vertical Burning Test" is adopted: it allows the classification of the materials at 94 V-0, 94 V-1 and 94 V-2 levels on the basis of the combustion time of the test pieces and on the basis of whether they do or do not gibr off on drop inflamed particles. According to said method, the test piece is primed, while maintained in vertical position, by approaching the flame at its extreme end, and performing two ignition attempts, each of them lasting 10 seconds Each test is performed on a group of 5 test pieces, and also measuring the time to extinguishment for 4 subsequent ignitions on the same test piece, as further differentiating criterion.

TABLE 1

| COMPONENTS (PERCENT BY WEIGHT) | | | | | | | | | | | |
|---|---|---|---|---|---|---|---|---|---|---|---|
| POLYPROPYLENE (FLAKES F) | COMPLEMENT TO 100 | | | | | | | | | | |
| DICYANDIAMIDE.BiBr$_3$ (EX. 1) | 0.1 | 0.3 | 0.5 | 1 | 2 | — | — | — | — | — | — |
| DICYANDIAMIDE.BiCl$_3$ (EX. 2) | — | — | — | — | — | 4 | 10 | — | — | — | — |
| DICYANDIAMIDE.SbBr$_3$ (EX. 3) | — | — | — | — | — | — | — | 1 | 3 | — | — |
| ACETOGUANAMINE.SbBr$_3$ (EX. 8) | — | — | — | — | — | — | — | — | — | 0.5 | — |
| MELAMINE.BiBr$_3$ (EX. 6) | — | — | — | — | — | — | — | — | — | — | 0.5 |
| INTEROX CC DFB (VP-1700)* | 0.2 | 0.2 | 0.2 | 0.2 | 0.2 | 0.2 | 0.2 | 0.2 | 0.2 | 0.3 | 0.3 |
| IRGANOX 1010 (STABILISER) | 0.1 | 0.1 | 0.1 | 0.1 | 0.1 | 0.1 | 0.1 | 0.1 | 0.1 | 0.1 | 0.1 |
| TPS (STABILISER) | 0.2 | 0.2 | 0.2 | 0.2 | 0.2 | 0.2 | 0.2 | 0.2 | 0.2 | 0.2 | 0.2 |
| PROPERTIES OF THE PRODUCTS | | | | | | | | | | | |
| OXYGEN INDEX | 26.5 | 30.5 | 31 | 31.8 | 32.4 | 25.5 | 27.5 | 26 | 27.5 | 29 | 29.5 |
| UL - 94 (3 mm) | V-2 | V-2 | V-2 | V-2 | V-2 | B | V-2 | B | V-2 | V-2 | V-2 |
| EXTINCTION TIMES FOR | 12/15 | 6/4 | ⅜ | 1/1 | 1/1 | — | 7/5 | — | 25/15 | 3/1 | 2/1 |
| 4 SUBSEQUENT IGNITIONS | 13/14 | 4/3 | ⅜ | 2/1 | 1/1 | — | 8/3 | — | 10/12 | ⅜ | 2/2 |

TABLE 1-continued

| COMPONENTS (PERCENT BY WEIGHT) |
|---|
| (seconds) |

B = burns
V-2 = stops combustion in 30 seconds dropping inflamed particles
*2,3-dimethyl-2,3-diphenylbutane

TABLE 2

| COMPONENTS (PERCENT BY WEIGHT) | | | | | | | | | |
|---|---|---|---|---|---|---|---|---|---|
| POLYPROPYLENE (FLAKES F) | COMPLEMENT TO 100 | | | | | | | | |
| DICYANDIAMIDE.BiBr$_3$ (EX. 1) | 0.5 | 0.5 | 0.5 | 0.5 | 0.5 | 3 | 5 | 10 | — |
| PRODUCT OF EXAMPLE 7 | — | — | — | — | — | — | — | — | 0.5 |
| INTEROX CC DFB (VP-1700)* | — | 0.1 | 0.2 | 0.3 | 0.5 | — | — | — | 0.3 |
| IRGANOX 1010 (STABILISER) | 0.1 | 0.1 | 0.1 | 0.1 | 0.1 | 0.1 | 0.1 | 0.1 | 0.1 |
| TPS (STABILISER) | 0.2 | 0.2 | 0.2 | 0.2 | 0.2 | 0.2 | 0.2 | 0.2 | 0.2 |
| PROPERTIES OF THE PRODUCTS | | | | | | | | | |
| OXYGEN INDEX | 20 | 27 | 31 | 32 | 33 | 24 | 27 | 29.2 | 30 |
| UL - 94 (3 mm) | B | V-2 | V-2 | V-2 | V-2 | B | V-2 | V-2 | V-2 |
| EXTINCTION TIMES FOR 4 | — | 5/4 | ¾ | 1/1 | ½/½ | — | ⅞ | ½ | ⅔ |
| SUBSEQUENT IGNITIONS | — | 5/3 | ¾ | 1/1 | 1/½ | — | 5/9 | ½ | 3/1 |
| (seconds) | | | | | | | | | |

B = burns
V-2 = stops combustion in 30 seconds dropping inflamed particles
*2,3-dimethyl-2,3-diphenylbutane

TABLE 3

| COMPONENTS (PERCENT BY WEIGHT) | | | | | | | |
|---|---|---|---|---|---|---|---|
| POLYSTYRENE (CRYSTAL) | 100 | 99 | — | — | — | — | — |
| POLYSTYRENE (HIPS) | — | — | 85 | — | — | — | — |
| NYLON 6 | — | — | — | 100 | 99 | — | — |
| ABS* | — | — | — | — | — | 100 | 80 |
| MELAMINE.BiBr$_3$ | — | 0.7 | 15 | — | 0.7 | — | 20 |
| INTEROX CC DFB (VP-1700)** | — | 0.3 | — | — | 0.3 | — | — |
| PROPERTIES OF THE PRODUCTS | | | | | | | |
| OXYGEN INDEX | 18 | 24.5 | 26 | 20 | 23 | 18.8 | 24.5 |
| UL - 94 (3 mm) | B | V-2 | V-0 | B | V-2 | B | V-0 |
| EXTINCTION TIMES FOR 4 | — | ½ | 3/3 | — | 1/1 | — | ¾ |
| SUBSEQUENT IGNITIONS | — | 2/1 | 2/4 | — | 2/1 | — | ⅔ |
| (seconds) | | | | | | | |

*BUTADIENE 15%, ACRYLONITRILE 25%, STYRENE 60%
B = burns
V-2 = stops combustion in 30 seconds dropping inflamed particles
V-0 = stops combustion in 5 seconds dropping inflamed particles
**2,3-dimethyl-2,3-diphenylbutane

TABLE 4

| COMPONENTS (PERCENT BY WEIGHT) | | | | | | | |
|---|---|---|---|---|---|---|---|
| POLYPROPYLENE (FLAKES F) | COMPLEMENT TO 100 | | | | | | |
| DICYANDDIAMIDE.BiBr$_3$ (EX. 1) | 0.5 | — | — | — | — | — | — |
| BiBr$_3$ | — | 0.5 | — | 0.4 | — | 0.4 | — |
| BiOBr | — | — | 0.5 | — | 0.4 | — | 0.4 |
| INTEROX CC DFB* | 0.3 | 0.3 | 0.3 | 0.3 | 0.3 | 0.3 | 0.3 |
| DICYANDIAMIDE | — | — | — | 0.1 | 0.1 | — | — |
| MELAMINE | — | — | — | — | — | 0.1 | 0.1 |
| IRGANOX 1010 (STABILIZER) | 0.1 | 0.1 | 0.1 | 0.1 | 0.1 | 0.1 | 0.1 |
| TPS (STABILIZER) | 0.2 | 0.2 | 0.2 | 0.2 | 0.2 | 0.2 | 0.2 |
| PROPERTIES OF THE PRODUCTS | | | | | | | |
| OXYGEN INDEX | 32 | 21 | 20.5 | 24.8 | 23.8 | 24 | 23.5 |
| UL - 94 (3 mm) | V-2 | B | B | B | B | B | B |
| EXTINCTION TIMES FOR 4 | 1/1 | — | — | — | — | — | — |
| SUBSEQUENT IGNITIONS | 1/1 | — | — | — | — | — | — |
| (seconds) | | | | | | | |

B = burns
V-2 = stops combustion in 30 seconds dropping inflamed particles
*2,3-dimethyl-2,3-diphenylbutane

What is claimed is:

1. Complexes of bismuth and antimony halides with amines having formula:

$$R \bullet (MeX_3)_y \qquad (I)$$

where
R is an amine selected from the group consisting of 2-guanidinobenzimidazole, isophoronediamine, dicyandiamide, guanamine, melamine, piperzine, all of which may be optionally substituted with an alkyl, aryl or acyl group and a compound prepared from dicyandiamide or melamine having from 2 to 9 triazine rings condensed or linked to each other through at least a —NH— group;
Me is bismuth or antimony;

X is chlorine or bromine; and y is a number comprised from 0.3 to 4.

2. Complexes according to claim 1, wherein $MeX_3$ is Bi tribromide or trichloride and R is selected from the group consisting of dicyandiamide, guanamine, melamine and a compound having from 2 to 9 triazine rings condensed or linked to each other through at least a —NH— group.

3. Complexes according to claim 1 where y is 1.

4. Complexes according to claim 2 where y is 1.

5. Process for preparing complexes or mixtures of complexes of bismuth and antimony of the formula R . $(MeX_3)_y$, where R is an amine selected from the group consisting of 2-guanidinobenzimidazole, isophoronediamine, dicyandiamide, guanamine, melamine, piperazine, all of which may be optionally substituted with an alkyl, aryl or acyl group and a compound prepared from dicyandiamide or melamine having from 2 to 9 triazine rings condensed or linked to each other through at least a —NH— group, Me is bismuth or antimony, X is chlorine or bromine and y is a number comprised from 0.3 to 4, comprising heating a mixture of a metal halide $(MeX_3)$ with the amine in an amount of at least 0.3 mole of metal halide per mole of the amine or per mole of primary amino groups when present in the amine.

6. Process according to claim 5, wherein the amine is reacted with the metal halide at a temperature between 50° C and 300° C.

7. Process according to claim 5 in which a solution or suspension of the amine is reacted with the metal halide at a temperature between 0° C. and above 100° C. and the product is recovered from the reaction medium.

8. Process according to claim 5 in which the amine is selected from the group consisting of dicyandiamide, guanamine and melamine, and the complex obtained is thermally treated at temperatures from 100° C. to about 300° C.

9. A polymer composition having flame self-extinguishing properties, comprising by weight:
   (a) 85–99.7% of a thermoplastic polymer,
   (b) 0.3–15% of a complex or a mixture of complexes of claim 1, and
   (c) from 0 to 1% of a free radical promoter provided that when (c) is 0%, component (b) is present in an amount of at least 3% by weight.

10. The polymer composition according to claim 9 in which the amount of component b) present is between 0.3% and 10% by weight.

11. The polymer composition according to claim 10 in which the amount of the component (b) present is between 0.3% and 3% by weight, and the amount of component (c) present is between 0.05% and 0.1% by weight when said component is an organic peroxide, and is between 0.1% and 1% by weight when said component is a non-peroxide free radical promoter.

12. The polymer composition according to claim 9 in which component (b) is an equimolar complex of melamine and a metal halide selected from the group consisting of antimony trihalide and bismuth trihalide.

13. The polymer composition according to claim 9 wherein component (a) is a crystalline polyolefin and component (b) contains an amine selected from the group consisting of dicyandiamide, melamine, the product of the cyclization of dicyandiamide, and the product of the condensation of melamine.

14. The polymer composition according to claim 12 wherein the crystalline polyolefin is polypropylene.

15. A polymer composition having flame self-extinguishing properties, comprising by weight:
   (a) 85–99.7% of a thermoplastic polymer,
   (b) 0.3–15% of a complex or a mixture of complexes of claim 2, and
   (c) from 0 to 1% of a free radical promoter provided that when (c) is 0%, component (b) is present in an amount of at least 3% by weight.

16. A polymer composition having flame self-extinguishing properties, comprising by weight:
   (a) 85–99.7% of a thermoplastic polymer,
   (b) 0.3–15% of a complex or a mixture of complexes of claim 3, and
   (c) from 0 to 1% of a free radical promoter provided that when (c) is 0%, component (b) is present in an amount of at least 3% by weight.

17. A polymer composition having flame self-extinguishing properties, comprising by weight:
   (a) 85–99.7% of a thermoplastic polymer,
   (b) 0.3–15% of a complex or a mixture of complexes of claim 4, and
   (c) from 0 to 1% of a free radical promoter that when (c) is 0%, component (b) is present in an amount of at least 3% by weight.

18. The polymer composition according to claim 15 wherein component (a) is a crystalline polyolefin and component (b) contains an amaine selected from the group consisting of dicyandiamide, melamine, the product of the cyclization of dicyandiamide, and the product of the condensation of melamine.

19. The polymer composition according to claim 16 wherein component (a) is a crystalline polyolefin and component (b) contains an amine selected from the group consisting of dicyandiamide, melamine, the product of the cyclization of dicyandiamide, and the product of the condensation of melamine.

20. Formed articles obtained from the compositions of claim 9.

* * * * *